US011663758B2

United States Patent
Bharkhada et al.

(10) Patent No.: US 11,663,758 B2
(45) Date of Patent: May 30, 2023

(54) SYSTEMS AND METHODS FOR MOTION ESTIMATION IN PET IMAGING USING AI IMAGE RECONSTRUCTIONS

(71) Applicant: Siemens Medical Solutions USA, Inc., Malvern, PA (US)

(72) Inventors: Deepak Bharkhada, Knoxville, TN (US); Vladimir Panin, Knoxville, TN (US); William Whiteley, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 387 days.

(21) Appl. No.: 17/248,056

(22) Filed: Jan. 7, 2021

(65) Prior Publication Data
US 2022/0215599 A1 Jul. 7, 2022

(51) Int. Cl.
*G06N 3/08* (2023.01)
*G06T 11/00* (2006.01)
*G06N 3/04* (2023.01)
*G01T 1/29* (2006.01)

(52) U.S. Cl.
CPC .......... *G06T 11/008* (2013.01); *G01T 1/2985* (2013.01); *G06N 3/04* (2013.01); *G06N 3/08* (2013.01); *G06T 2210/41* (2013.01)

(58) Field of Classification Search
CPC . G06T 11/008; G06T 2210/41; G01T 1/2985; G01T 1/1663; G06N 3/04; G06N 3/08; G06N 3/045; A61B 6/037; A61B 6/5211; A61B 6/5264
USPC ........................................................ 382/131
See application file for complete search history.

(56) References Cited

U.S. PATENT DOCUMENTS

| | | | |
|---|---|---|---|
| 9,990,741 B2 * | 6/2018 | Panin | A61B 6/5247 |
| 2017/0039706 A1 * | 2/2017 | Mikhno | G06T 11/003 |
| 2018/0096259 A1 * | 4/2018 | Andrews | G06V 10/82 |
| 2020/0187874 A1 | 6/2020 | Hayden | |
| 2020/0337591 A1 | 10/2020 | Rotman et al. | |
| 2020/0337592 A1 * | 10/2020 | Brada | G01R 33/4818 |
| 2020/0337666 A1 | 10/2020 | Kabus et al. | |
| 2020/0341100 A1 | 10/2020 | Heukensfeldt Jansen et al. | |
| 2020/0118669 A1 | 12/2020 | Mohr et al. | |

* cited by examiner

*Primary Examiner* — Charlotte M Baker

(57) ABSTRACT

A computer-implemented method for generating a motion corrected image is provided. The method includes receiving listmode data collected by an imaging system; producing two or more histo-image frames or two or more histo-projection frames based on the listmode data; providing the two or more histo-image frames or two or more histo-projection frames to an Artificial Intelligence (AI) system; receiving two or more AI reconstructed images from the AI system based on the two or more histo-image frames or the two or more histo-projection frames; and generating a motion estimation in reconstructed images by using a motion free AI reconstructed image frame as a reference frame.

23 Claims, 6 Drawing Sheets

SYSTEMS AND METHODS FOR MOTION ESTIMATION IN PET IMAGING USING AI IMAGE RECONSTRUCTIONS

TECHNICAL FIELD

Aspects of the present disclosure relate in general to medical diagnostic systems and, more particularly, to reconstructing images from nuclear imaging systems for diagnostic and reporting purposes in which a neural network is used to produce images upon which motion may be estimated for performing motion correction.

BACKGROUND

Nuclear imaging systems can employ various technologies to capture images. For example, some nuclear imaging systems employ positron emission tomography (PET) to capture images. PET is a nuclear medicine imaging technique that produces tomographic images representing the distribution of positron emitting isotopes within a body. PET acquisition requires scans of long duration, and a significant magnitude of patient motion during the scan is sometimes unavoidable. For example, the pattern caused by breathing may result in a relatively large displacement of organs and consequent blurring of clinically relevant PET features in regions affected by the motion.

To limit the effects of cyclic motion like respiratory motion, the PET data is separated by phases of the breathing cycle. The breathing pattern may be monitored either by external devices or by tracing the movement of objects in the list mode file domain of the PET data. Once the breathing pattern is established, the PET data is separated into gates according to the phase or amplitude of respiration. Each gate represents a particular (quasi) frozen phase of motion. The gate with minimally integrated motion is chosen to reconstruct the PET image. While the motion artifact is suppressed, however, image quality suffers from a greater amount of noise due to reconstruction from less than all the PET data.

To achieve motion artifact suppression and approach maximum signal-to-noise ratio (SNR), each frame/gate's data is individually reconstructed and registered to one of the reconstructions in the image domain. The aligned reconstructions (or images from the reconstructions) are then averaged. Another approach is to reconstruct one image from all available data through the incorporation of the field of motion into the reconstruction process (i.e., repeated each iteration of the reconstruction or in the forward and backward projection loop). This approach, however, is specific to certain applications in which the motion concerned with is cyclic and is not applicable to applications where the motion concerned with is non-cyclic motions that are generally not physiological. Thus, if a patient's motion during an image acquisition session involves both cyclic motion and non-cyclic motion, a separate motion correction methods are required to correct each type of motion.

Therefore, an improved method for implementing motion correction in nuclear imaging systems that can handle both cyclic as well as non-cyclic motions is desired.

SUMMARY

Systems and methods for reconstructing medical images that include a novel approach that implements motion correction of both cyclic as well as non-cyclic motions are disclosed. The new method estimates the patient body motion by creating multiple short frames of data sequence in the form of histo-image frames or histo-projection frames from listmode data collected by an imaging system, processing the short frames of histo-images or histo-projection frames via an artificial intelligence neural-network (AI) system to obtain reconstructed image frames with improved signal-to-noise ratio (SNR); identifying at least one motion free AI reconstructed image frame among the two or more AI reconstructed image frames as a reference image frame; and estimating motion in each of the remaining non-reference AI reconstructed image frames by comparing the image frame data of the non-reference AI reconstructed image frames to the image frame data of the reference image frame. Reference image frame may be different for different regions in the image. This approach can be applied to both cyclic and non-cyclic motions.

A computer-implemented method for generating a motion corrected image is provided. The method comprises receiving listmode data collected by an imaging system; producing two or more short frames of data in the form of histo-image frames or histo-projection frames based on the listmode data; providing the two or more histo-image frames or histo-projection frames to an AI system; receiving two or more AI reconstructed image frames from the AI system, wherein the AI reconstructed image frames are based on the two or more histo-image frames or histo-projection frames; identifying at least one motion free AI reconstructed image frame among the two or more AI reconstructed image frames as a reference image frame; and estimating motion in each of the remaining non-reference AI reconstructed image frames by comparing the image frame data of the non-reference AI reconstructed image frames to the image frame data of the reference image frame.

Also provided is a system comprising: a non-transitory memory storing listmode data received from an imaging device and a set of instructions stored thereon; and at least one processor communicatively coupled to the memory and configured to execute the set of instructions to: produce two or more histo-image frames or histo-projection frames based on events and corresponding time-of-flight (TOF) data and an approximation algorithm; provide the two or more histo-image frames or two or more histo-projection frames to a neural network; receive two or more AI reconstructed image frames having been processed by the neural network; identify at least one motion free AI reconstructed image frame among the two or more AI reconstructed image frames as a reference image frame; and estimate motion in each of the remaining non-reference AI reconstructed image frames by comparing the image frame data of the non-reference AI reconstructed image frames to the image frame data of the reference image frame.

Also provided is a non-transitory computer readable medium storing instructions that, when executed by at least one processor, cause the at least one processor to perform operations comprising: receiving listmode data collected by an imaging system; producing two or more histo-image frames or histo-projection frames based on the listmode data; providing the two or more histo-image frames or histo-projection frames to an AI system; receiving two or more AI reconstructed image frames from the AI system based on the two or more histo-image frames or the two or more histo-projection frames; identifying at least one motion free AI reconstructed image frame among the two or more AI reconstructed image frames as a reference image frame; and estimating motion in each of the remaining non-reference AI reconstructed image frames by comparing the image frame data of the non-reference AI reconstructed image frames to the image frame data of the reference image frame.

BRIEF DESCRIPTION OF THE DRAWINGS

The following will be apparent from elements of the figures, which are provided for illustrative purposes and are not necessarily drawn to scale.

DETAILED DESCRIPTION

This description of the exemplary embodiments is intended to be read in connection with the accompanying drawings, which are to be considered part of the entire written description.

The exemplary embodiments are described with respect to the claimed systems as well as with respect to the claimed methods. Furthermore, the exemplary embodiments are described with respect to methods and systems for image reconstruction, as well as with respect to methods and systems for training functions used for image reconstruction. Features, advantages, or alternative embodiments herein can be assigned to the other claimed objects and vice versa. For example, claims for the providing systems can be improved with features described or claimed in the context of the methods, and vice versa. In addition, the functional features of described or claimed methods are embodied by objective units of a providing system. Similarly, claims for methods and systems for training image reconstruction functions can be improved with features described or claimed in context of the methods and systems for image reconstruction, and vice versa.

Various embodiments of the present disclosure can employ machine learning methods or processes to provide clinical information from nuclear imaging systems. For example, the embodiments can employ machine learning methods or processes to reconstruct images based on captured measurement data, and provide the reconstructed images for clinical diagnosis. In some embodiments, neural network processing may be implemented to produce images of sufficient quality to enable a system to estimate motion vectors for use in motion correction.

In some embodiments, a scanning device, such as a positron emission tomography (PET) scanner, provides measurement data, such as three-dimensional (3D) TOF projection data. The projection data may be provided to a neural network processing system for producing reconstructed images for use in estimating motion vectors. The estimated motion vectors may be used by a reconstruction device to reconstruct an image with motion correction.

Figure 1:
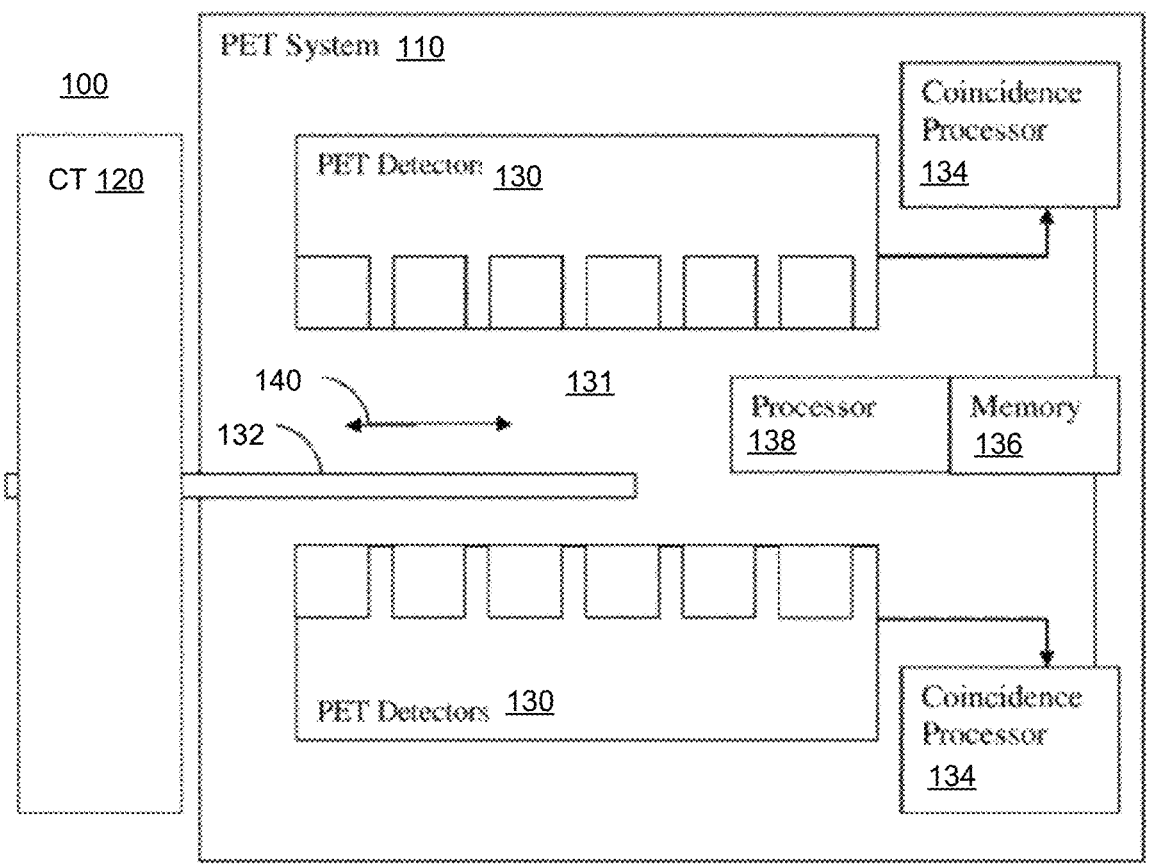
FIG. 1 illustrates a medical system, in accordance with some embodiments.

FIG. 1 shows an imaging system 100 for motion correction in TOF PET. The imaging system 100 implements the disclosed methods and/or other methods according to some embodiments. The imaging system 100 includes PET system 110 and a computed tomography (CT) scanner 120. In other embodiments, the imaging system 100 may include only the PET system 110, or may alternatively or additionally include a magnetic resonance (MR), ultrasound, optical (e.g., camera), or other type of scanner.

The PET system 110 includes rings of detectors 130, a bed 132, coincidence processors 134, a memory 136, and a processor 138. In FIG. 1, the rings of detectors 130 are schematically shown in a cross-sectioned view to show the provision of the patient bed 132 in the patient tunnel 131 of the PET system 110. The processor 138, memory 136, and/or a display can be part of the PET system 110 or can be separate (e.g., a computer or workstation). Additional, different, or fewer components may be provided. As another example, the imaging system 100 includes power supplies, communications systems, and user interface systems.

The patient bed 132 may be a gurney, table, or other support to hold an examination subject, such as a patient. A robot, gears, cable, track, rollers, and/or other device move or allow movement of the bed 132. The movement is along an axial dimension, the longitudinal axis, represented by double arrow 140. In alternative embodiments, the bed 132 is fixed relative to the detectors 130. Continuous bed motion mode, step-and-shoot mode, or single bed position mode may be used. The detectors 130 and/or PET system 110 form the patient tunnel 131 through which the bed 132 holds or moves the patient. The distance from the longitudinal axis of this bore is the radial distance. The angle about the axial axis is the azimuth. Other coordinate systems, such as a cylindrical or polar coordinate system, may be used.

The PET detectors 130 may be crystals or other photon detectors. For example, the detectors 130 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

The detectors 130 are arranged individually or in groups. Blocks or groups of detectors 130 are arranged in any pattern around the bore. In an exemplary embodiment, blocks of detectors 130 may be arranged as separate rings around the bore. The rings may be spaced apart, but are generally placed adjacent or abutting each other. Any gap may be provided between blocks within a ring, detectors within a block, and/or between rings. Any number of detectors in a block (e.g., 8 or 16), detector blocks in a ring, and/or rings may be used. The rings may extend completely or only partially around the bore.

The PET system 110 is a nuclear imaging system. The detectors 130 can be used to perform a PET scan along a line of response (LOR) between the detectors 130. The detectors 130 detect gamma rays emitted indirectly by a positron-emitting tracer. Pairs of gamma rays generated by a same positron may be detected using the ring of the detectors 130. The pairs of gamma rays travel about 180 degrees apart. If the direction of travel intersects the arrangement of detectors 130 at two locations, a coincident pair may be detected. To distinguish specific pairs, the coincidence of detected gamma rays is determined. The timing of receipt is used to pair the detected gamma rays. The timing, as prompt data, also indicates the TOF, providing information about where along a LOR the emission occurred. This TOF data is parameterized by LOR and time defining location along the LOR, providing a histogram-image of distribution of emissions by location (LOR and position along LOR).

Each individual detection output from the detectors 130 can include energy, position, and timing information. Alternatively, the detectors 130 output energy information and a receiving processor determines the timing and position (e.g., based on port assignment or connections). The timing information is used to determine coincidence of detection by different detectors by the coincidence processors 134 as well as general position along the LOR of the emission. Pairs of gamma rays associated with a same positron emission are determined by the coincidence processors 134. Based on the detected event, the LOR and TOF is determined, given the detectors involved in the detection of that event.

The coincidence processors 134 and/or the processor 138 categorize the detected events relative to a physiological cycle. For example, a breathing cycle is divided into any number (e.g., 8) of phases. Based on the time of occurrence relative to a breathing cycle measured with the sensor, counts for each bin (e.g. location along each LOR) are maintained separately for each phase.

The detected events are passed to the memory 136 and/or processor 138. The processor 138 connects with the detectors 130, such as through the coincidence processors 134. The processor 138 can be, for example, a general processor, digital signal processor, graphics processing unit, application specific integrated circuit, field programmable gate array, digital circuit, analog circuit, or combinations thereof. The processor 138 can be a single device, a plurality of devices, or a network. For more than one device, parallel or sequential division of processing may be used. Different devices making up the processor 138 may perform different functions. In one embodiment, the processor 138 is a control processor or other processor of the imaging system 100 or the PET system 110. In other embodiments, the processor 138 is part of a separate workstation or computer. According to disclosed embodiments, the processor 138 operates pursuant to stored instructions to perform various acts described herein. The processor 138 is configured by software, firmware, and/or hardware.

The processor 138 can be configured to apply motion correction to data representing the detection of the LOR and TOF (together the TOF data). The motion correction can be applied prior to producing a final image reconstruction. The motion correction can account for respiratory, cardiac or brain motion, for example. Motion correction methods may rely on motion vector estimations prior to performing a motion correction to produce a final image reconstruction. Disclosed embodiments can include systems and methods for producing motion estimations based on AI image reconstructions produced by a neural network. The processor 138 can be configured to use known methods to produce motion corrected data from the motion estimation and generate a final reconstructed image from the motion corrected data. The final reconstructed image may be a three-dimensional rendering, for example.

Data, such as TOF data, phase information, attenuation information, normalization information, motion vector estimations, projection of the motion, motion corrected data, reconstructed image, or other data may be stored in the memory 136. The data can be stored in any format. The memory 136 may be a buffer, cache, RAM, removable media, hard drive, magnetic, optical, database, or other now known or later developed memory. The memory 136 may be a single device or group of two or more devices. The memory 136 is part of the PET system 110 or a remote workstation or database, such as a PACS memory.

The memory 136 is additionally or alternatively a non-transitory computer readable storage medium with processing instructions. The memory 136 stores data representing instructions executable by the programmed processor 138. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The PET system 110 may include a display. For example, the processor 138 can reconstruct the patient or object being scanned from motion corrected data. The reconstruction can be used for three-dimensional rendering, multi-planar reconstruction, or two-dimensional imaging of the function of the tissue of the patient. The images can be displayed on the display. The display can be a CRT, LCD, plasma screen, projector, printer, or other output device for showing an image.

Figure 2:
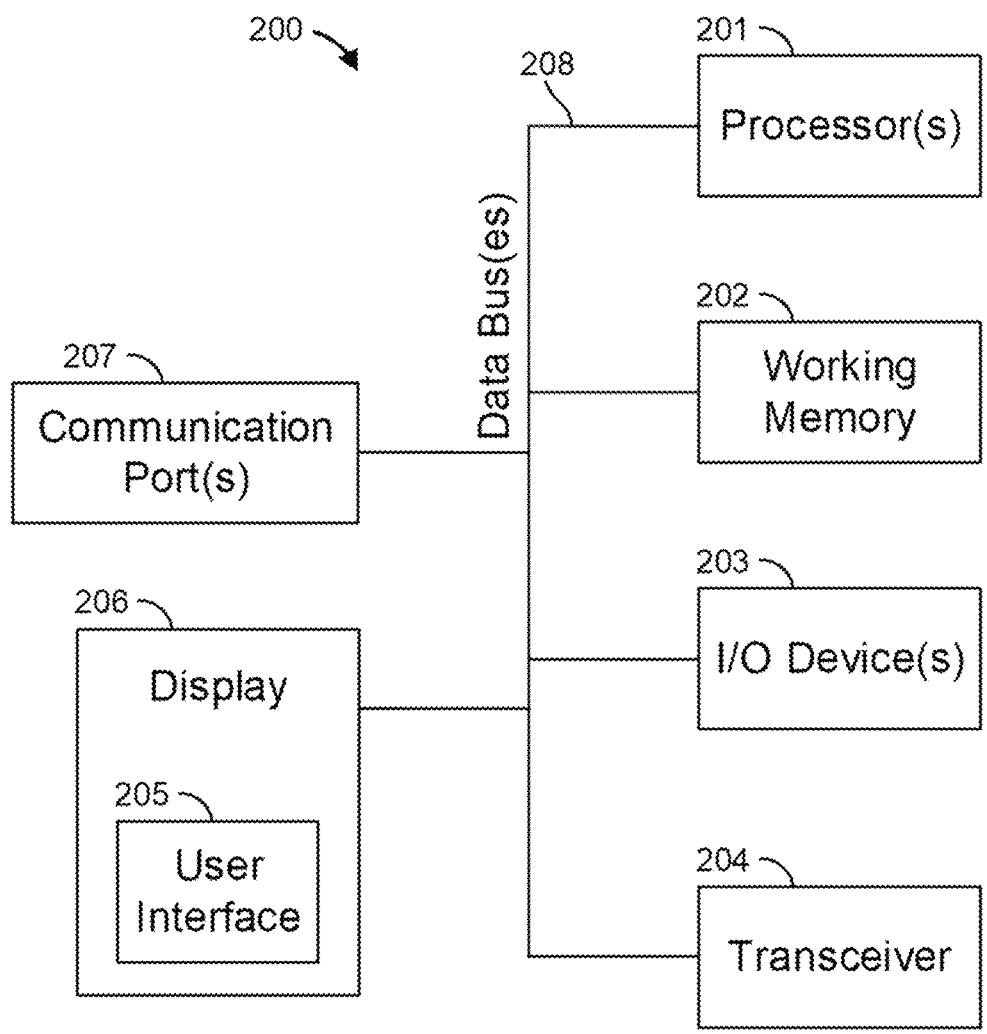
FIG. 2 illustrates a block diagram of an example computing device that can perform one or more of the functions described herein, in accordance with some embodiments.

FIG. 2 illustrates a computing device 200 that can be employed by the imaging system 100. Computing device 200 can implement, for example, one or more of the functions described herein. For example, computing device 200 can implement one or more of the functions of imaging system 100, such as image reconstruction processes related to data gathered by the PET system 110 and/or the CT system 120.

Computing device 200 can include one or more processors 201, working memory 202, one or more input/output devices 203, instruction memory 207, a transceiver 204, one or more communication ports 207, and a display 206, all operatively coupled to one or more data buses 208. Data buses 208 allow for communication among the various devices. Data buses 208 can include wired, or wireless, communication channels.

Processors 201 can include one or more distinct processors, each having one or more cores. Each of the distinct processors can have the same or different structure. Processors 201 can include one or more central processing units (CPUs), one or more graphics processing units (GPUs), application specific integrated circuits (ASICs), digital signal processors (DSPs), and the like. Processors 201 may correspond to the processor 138 of the PET system 110.

Processors 201 can be configured to perform a certain function or operation by executing code, stored on instruction memory 207, embodying the function or operation. For example, processors 201 can be configured to perform one or more of any function, method, or operation disclosed herein. The memory 207 may correspond to the memory 136 of the PET system 110.

Instruction memory 207 can store instructions that can be accessed (e.g., read) and executed by processors 201. For example, instruction memory 207 can be a non-transitory, computer-readable storage medium such as a read-only memory (ROM), an electrically erasable programmable read-only memory (EEPROM), flash memory, a removable disk, CD-ROM, any non-volatile memory, or any other suitable memory. For example, instruction memory 207 can store instructions that, when executed by one or more processors 201, cause one or more processors 201 to perform one or more of the functions of image reconstruction system 104.

Processors 201 can store data to, and read data from, working memory 202. For example, processors 201 can store a working set of instructions to working memory 202, such as instructions loaded from instruction memory 207. Processors 201 can also use working memory 202 to store dynamic data created during the operation of computing device 200. Working memory 202 can be a random access memory (RAM) such as a static random access memory (SRAM) or dynamic random access memory (DRAM), or any other suitable memory.

Input-output devices 203 can include any suitable device that allows for data input or output. For example, input-output devices 203 can include one or more of a keyboard, a touchpad, a mouse, a stylus, a touchscreen, a physical button, a speaker, a microphone, or any other suitable input or output device.

Communication port(s) 207 can include, for example, a serial port such as a universal asynchronous receiver/transmitter (UART) connection, a Universal Serial Bus (USB) connection, or any other suitable communication port or connection. In some examples, communication port(s) 207 allows for the programming of executable instructions in instruction memory 207. In some examples, communication port(s) 207 allow for the transfer (e.g., uploading or downloading) of data, such as sinograms (e.g., sinogram data 103) and attenuation maps (e.g., attenuation maps 105).

Display 206 can display user interface 205. User interfaces 205 can enable user interaction with computing device 200. For example, user interface 205 can be a user interface for an application that allows for the viewing of final images generated by imaging system 100. In some examples, a user can interact with user interface 205 by engaging input-output devices 203. In some examples, display 206 can be a touchscreen, where user interface 205 is displayed on the touchscreen.

Transceiver 204 allows for communication with a network, such as a Wi-Fi network, an Ethernet network, a cellular network, or any other suitable communication network. For example, if operating in a cellular network, transceiver 204 is configured to allow communications with the cellular network. Processor(s) 201 is operable to receive data from, or send data to, a network via transceiver 204.

Figure 3:
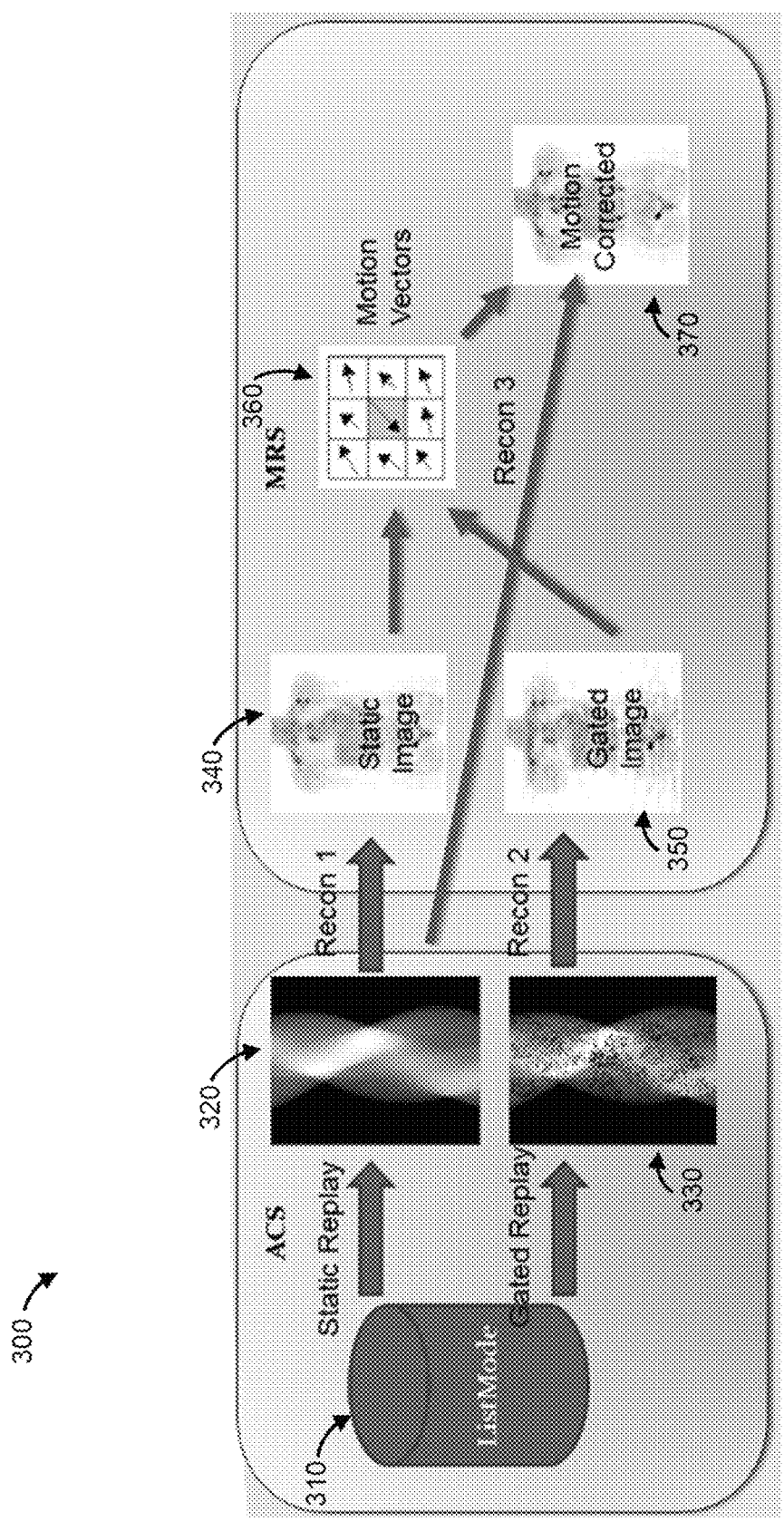
FIG. 3 illustrates a diagram of a prior art reconstruction process for cyclic motion correction, in accordance with previous image reconstruction systems.

FIG. 3 illustrates a diagram of a prior art image reconstruction process 300. An Acquisition Computer System (ACS) is a software and computing subsystem that collects raw nuclear imaging listmode data from the PET scanner and organizes it into projections 320 and 330. The Molecular Reconstruction System (MRS) is a software and computing subsystem that uses the projections to reconstruction images 340 and 350. The MRS also calculates motion vectors 360 from the reconstructed images 340 and 350 enabling it to produce a motion corrected final image 370. The process 300 may be performed by a system configured to execute a plurality of steps to convert data collected by imaging system 100 into one or more medical images for use in analysis and diagnosis of a patient. The imaging system 100 collects data in the form of listmode data 310. The listmode data 310 can include data collected by the PET system 110.

In the image reconstruction process 300, the listmode data 310 is converted into images while taking into account potential motion errors by performing gating and motion correction steps. For instance, the PET system 110 or computing device 200 uses the listmode data 310 to generate a static sinogram 320 and a gated sinogram 330. The detector crystals, also referred to as scintillators, convert the energy of a gamma ray into a flash of light that is sensed by the detector PMT or silicon photo multiplier (SiPM). In coincidence mode, a gamma ray pair detected within a coincidence time by a pair of PET detectors is recorded by the PET scanner as an annihilation event. During a patient scan, hundreds of millions of events are typically detected and recorded. Due to the approximate 180 degree angle of departure from the annihilation site, the location of the two detectors registering the event define the LOR passing through the location of the annihilation. Detection of the LORs is performed by a coincidence detection scheme. A valid event line is registered if both photons of an annihilation are detected within a coincidence window of time. Coincidence detection methods ensure that an event is histogrammed only if both photons originate from the same positron annihilation. The observed events are sorted and organized with respect to each of a plurality of projection rays from the listmode data 310. By plotting these lines of response, a sinogram is produced that may be used by, for example, a process to produce a three dimensional image of the activity. All events occurring along each projection ray may be organized into one bin of a three-dimensional sinogram array. The array may be stored in a computer-readable memory media.

The prior art image reconstruction process 300 can further include the PET system 110 (e.g., by computing device 200) producing a static reconstruction 340 from the static sinogram 320 and a gated reconstruction 350 from the gated sinogram 330. The PET system 110 is configured to estimate motion vectors from the static reconstruction 340 and the gated reconstruction 350 using known motion vector estimation techniques to generate a motion vector field 360. The motion vector field 360 includes information about the motion of the patient during data collection and can be used to correct a final image by accounting for that motion. The PET system 110 is further configured to generate a reconstructed image 370 based on, for example, the static sinogram 320 and the motion vector field 360. The PET system 110 may perform an image reconstruction using the static sinogram 320 and the motion vector field 360 to produce a motion corrected reconstructed image 370.

As described above in relation to the image reconstruction process 300, the motion vectors are calculated from reconstruction images of the gated sinogram(s) and static sinogram(s). These reconstructions steps take about the same reconstruction time as a regular reconstruction and the final processing time can be longer than 3 times of a regular reconstruction. In addition, the generation of gated sinogram also takes substantial time.

Figure 4:
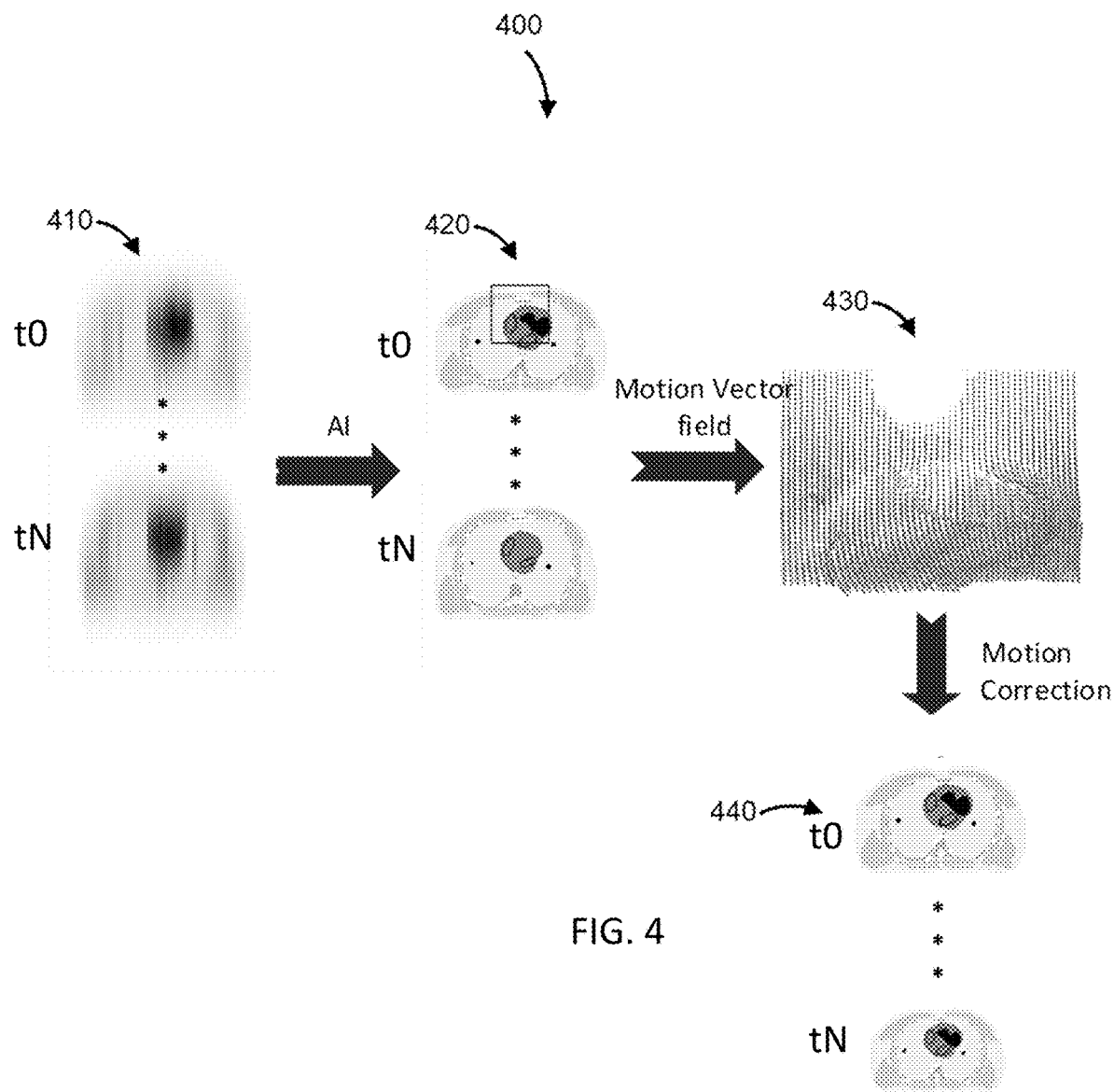
FIG. 4 illustrates a general process for using artificial intelligence (AI) to produce motion correction data, in accordance with some disclosed embodiments.

FIG. 4 is a diagram of an image reconstruction process 400 according to some embodiments of the present disclosure that can apply motion correction to mitigate effects of the patient body motion that may occur during imaging data acquisition session. The image reconstruction process 400 generates motion corrected images 440 using AI processing of the static and framed images from the scan data that is generated as multiple (two or more) short frames in the form of histo-image frames 410 or histo-projection frames. Time sequence notation "t0" to "tN" in FIG. 4 denotes the frames of data.

The histo-image frames 410 can be generated, for example, by the computing device 200 based on listmode data collected by the PET system 110. The histo-image frames 410, according to one embodiment, are approximations of visual representation of the listmode data (e.g., event data and corresponding TOF data) and an approximating algorithm. In an exemplary embodiment, the approximating algorithm can be a most-likely annihilation (MLA) algorithm to estimate data points for the histo-image frames 410. The MLA algorithm takes individual PET annihilation events and based on their TOF property, increments the most likely annihilation originating image pixel in either a histo-image data format, which is identical to the final image geometry, or a histo-projection data format, which is similar but contains only the events along angle of response under consideration. Histo-projections sampling grid is aligned with angle of response with elongated voxel size in TOF direction. MLA algorithm is also used to deposit event of particular angle f response into histo-projection voxel.

The histo-image frames 410, which provide an approximation of a visual representation of the listmode data, and histo-projection frames may not be sufficiently robust to estimate motion vectors. For example, the histo-image frames 410 may include excessive noise such that further processing is necessary to reduce SNR in order to effectively utilize the histo-image frames 410. To reduce SNR and improve quality, the two or more histo-image frames or two or more histo-projection frames are fed through an AI processing step to produce AI reconstructed image frames 420. The term "AI reconstructed images," as used herein, may generally refer to images produced using an AI algorithm, such as those produced by a neural network. For instance, the histo-image frames 410 or the histo-projection frames may be inputted to a neural network trained to refine PET histo-image frames or PET histo-projection frames. This process requires a properly trained convolutional neural network able to reconstruct histo-image frames or histo-projection frames into final image frames. This neural network training requires a sufficient training, validation and test data set, a properly configured convolutional neural network and a loss function designed to maximize the quality of the reconstructed images. In an exemplary embodiment, the neural network may be associated with a "FastPET" process such as that described in U.S. patent application Ser. No. 16/591,992 entitled "PET Image Reconstruction Using TOF Data and Neural Network," filed Oct. 3, 2019, the contents of which is hereby incorporated by reference in its entirety. The neural network processing performed by the PET system 110 produces reconstructed images 420.

Through the AI processing step, each frame data of the histo-image frames 410 are converted into AI reconstructed image frames 420. Next, the PET system 110 identifies at least one of the AI reconstructed image frames 420 that is motion free as a reference frame. Then, the PET system 110 compares the image frame data all of the other non-reference AI reconstructed image frames to the image frame data of the reference frame and estimates motion vectors for the non-reference AI reconstructed image frames 420 to generate a motion estimation in the form of a motion vector field 430 for each of the non-reference AI reconstructed image frames 420. This provides estimation of any patient motion in each of the non-reference AI reconstructed image frames in the form of a motion vector field 430 for each of the AI reconstructed image frame.

The motion free AI reconstructed image frame can be identified by using a number of different methods known to those skilled in the art. One example is center of distribution (COD) method to scrutinize the histo-image center of mass for each of the AI reconstructed image frame data to determine whether any portion of the image frame moved during the time segment that generated the histo-image. Another example is intensity variation method to scruitinize the histo-image for each of the AI reconstructed image frame data.

In some embodiments, the whole histo-image frame can be scruitinized for motion and use the whole histo-image frame that is motion free as a reference frame to detect and correct for motion in the non-reference AI reconstructed image frames. In other embodiments, some minimum number of regions within a histo-image frame can be scruitinized to detect motion and if no motion is detected in those regions, the histo-image frame can be used as a reference frame to detect and correct for motion in those regions in the non-reference AI reconstructed image frames. In some embodiments, if multiple motions in different regions are being considered, different histo-image frame can be used as a reference frame for each of the different regions of interest.

The motion vector field 430 can include information about the motion, if any, of the patient during the imaging data acquisition session based on the AI reconstructed images 420. The PET system 110 thereafter uses the set of motion vector fields 430 to perform a motion correction on the corresponding frames and generate one or more motion-corrected reconstructed image frames 440. This motion vector can be used to correct motion using existing approaches one of which is to apply motion correction in projection space on the histo-image frames or histo-projection frames for motion before reconstruction or directly apply motion correction to AI reconstructed images to obtain motion corrected reconstructed images. For example, the PET system 110 (e.g., via the computing device 200) can apply motion correction methods to the listmode data, histo-image frames 410, and/or AI reconstructed image frames 420 based on the motion estimation (e.g., motion vector field) to generate motion-corrected image frames 440 which can be used for motion corrected image reconstruction. As illustrated in FIG. 4, the AI reconstructed image frames 420 corresponding to the time sequence t0 to tN are processed through this motion correction process and resulted in the motion corrected reconstructed image frames 440 for the time sequence t0 to tN.

The process 400 is beneficial because only one reconstruction process is implemented to produce a final image of sufficient quality for reliable use in diagnostics. This is in contrast to the prior art process 300 in which additional reconstruction per frame is required for motion estimation. These reconstructed images may be very noisy and for very short frames may not permit motion estimations. As image reconstruction processes are generally time-consuming, the process 400 is able to produce final images in a reduced timeframe as compared to prior art methods. The use of a neural network to generate quality images, upon which a motion vector field for motion correction can be reliably produced, contributes to the time savings while maintaining and providing high quality and reliability to the process.

Figure 5:
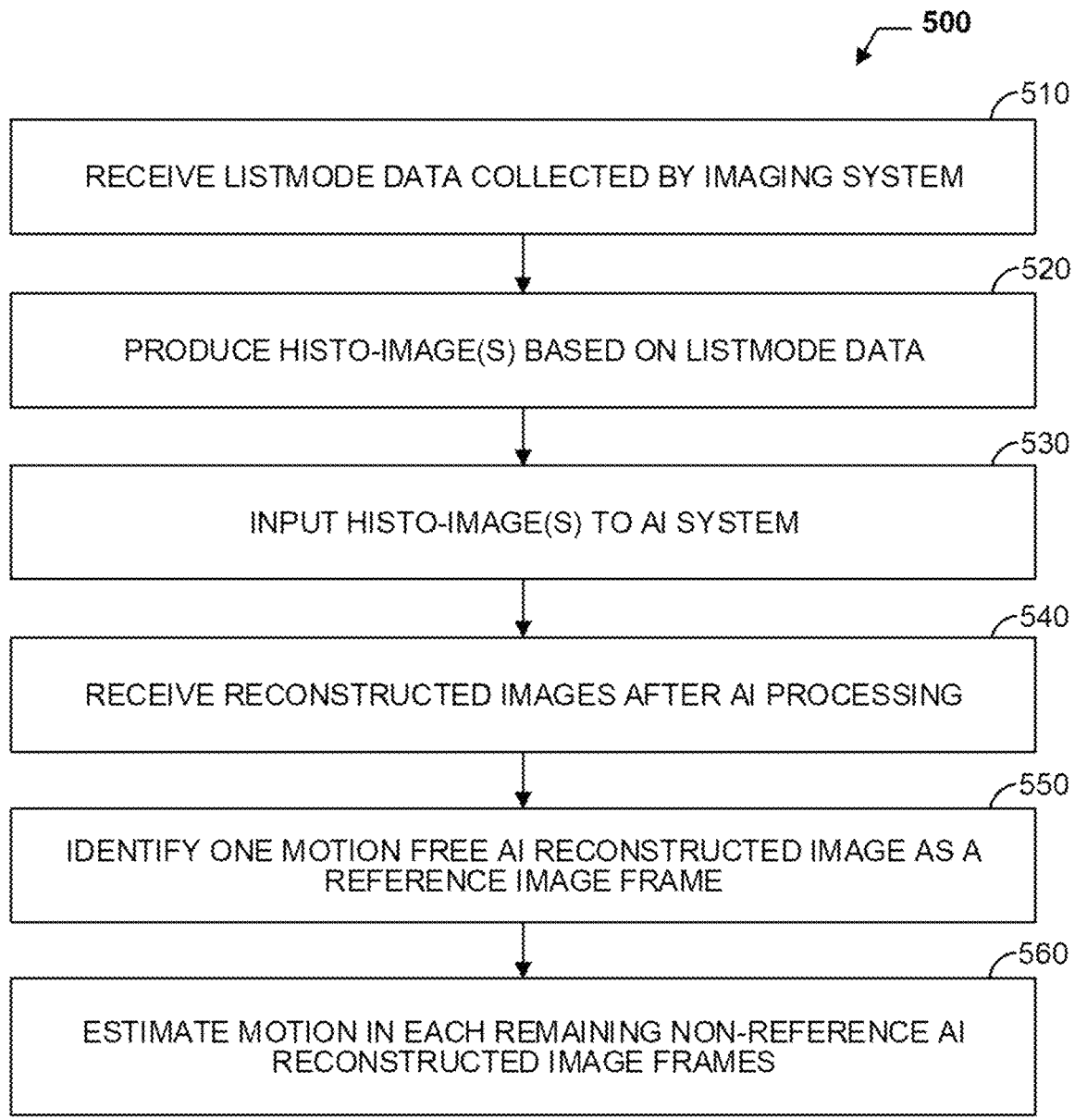
FIG. 5 is a flowchart of an example method to reconstruct an image, in accordance with some embodiments of the present disclosure.

FIG. 5 is a flowchart of another embodiment of an image reconstruction process 500 for generating a reconstructed image based on data collected by a PET scanner, such as the PET system 110 in the imaging system 100. One or more processors (e.g., processor 138 and/or processor 201) may be configured to execute software instructions to perform one or more steps of the process 500.

In step 510, the processor receives listmode data collected by the imaging system 100. The imaging system 100 may perform, for example, a PET scan using the PET system 110 to produce the listmode data. The listmode data may be a data representation of a part of the body scanned by the imaging system 100 and for which a final image may be desired for analysis and/or diagnostic use.

In step 520, the processor produces a histo-image based on the listmode data. The histo-image may be an image produced based on an approximation algorithm applied to the listmode data, such as by inputting event and/or TOF data to the approximation algorithm. The histo-image, in some embodiments, may be different than a sinogram that may be conventionally generated based on listmode data. The processor may apply the approximation algorithm, which, in an exemplary embodiment, is a most likely annihilation (MLA) algorithm. In some embodiments, the processor may generate a plurality of histo-images. In other embodiments, the histo-images may be activity estimations or other data representations based on listmode data.

In step 530, the processor inputs one or more histo-images to an AI system to improve the quality of the one or more histo-images. For example, the processor may provide the histo-images to a neural network trained to improve the quality of the histo-image. The result may be considered an "AI reconstructed image." For example, the neural network may de-noise the histo-image based on being trained on other de-noised histo-images. In an exemplary embodiment, the neural network is associated with the "FastPET" system incorporated herein by reference. In an exemplary embodiment, the AI processing of the histo-images is quicker than a conventional image reconstruction process. For instance, the process of applying a neural network to a histo-image may take less than 1 second to produce an AI reconstructed image. In step 540, the processor receives the AI reconstructed images from the neural network. It should be understood that the neural network may be associated locally with the imaging system 100 or may be a remote computing component in communication with the imaging system 100.

In step 550, the processor identifies one motion free AI reconstructed image among the two or more AI reconstructed images as a reference image frame.

Then, in step 560, the processor estimates motion in each of the remaining non-reference AI reconstructed image frames by comparing the image frame data of the non-reference AI reconstructed image frames to the image frame data of the reference image frame. In preferred embodiments, the processor generates a motion vector field for each of the non-reference AI reconstructed image frame based on the estimated motion in each of the remaining non-reference AI reconstructed image frames. This motion vector can be used to correct motion using existing approaches one of which is to correct the histo-image or histo-projections frames for motion before reconstruction or directly apply motion correction to AI reconstructed images to obtain motion corrected reconstructed imagesNext, the processor applies motion correction to each of the non-reference AI reconstructed image frames using the corresponding motion vector field to generate motion corrected reconstructed image frames.

Once the motion corrected reconstructed image frames are generated, the imaging system 100 may display the final reconstructed image to a user.

Figure 6:
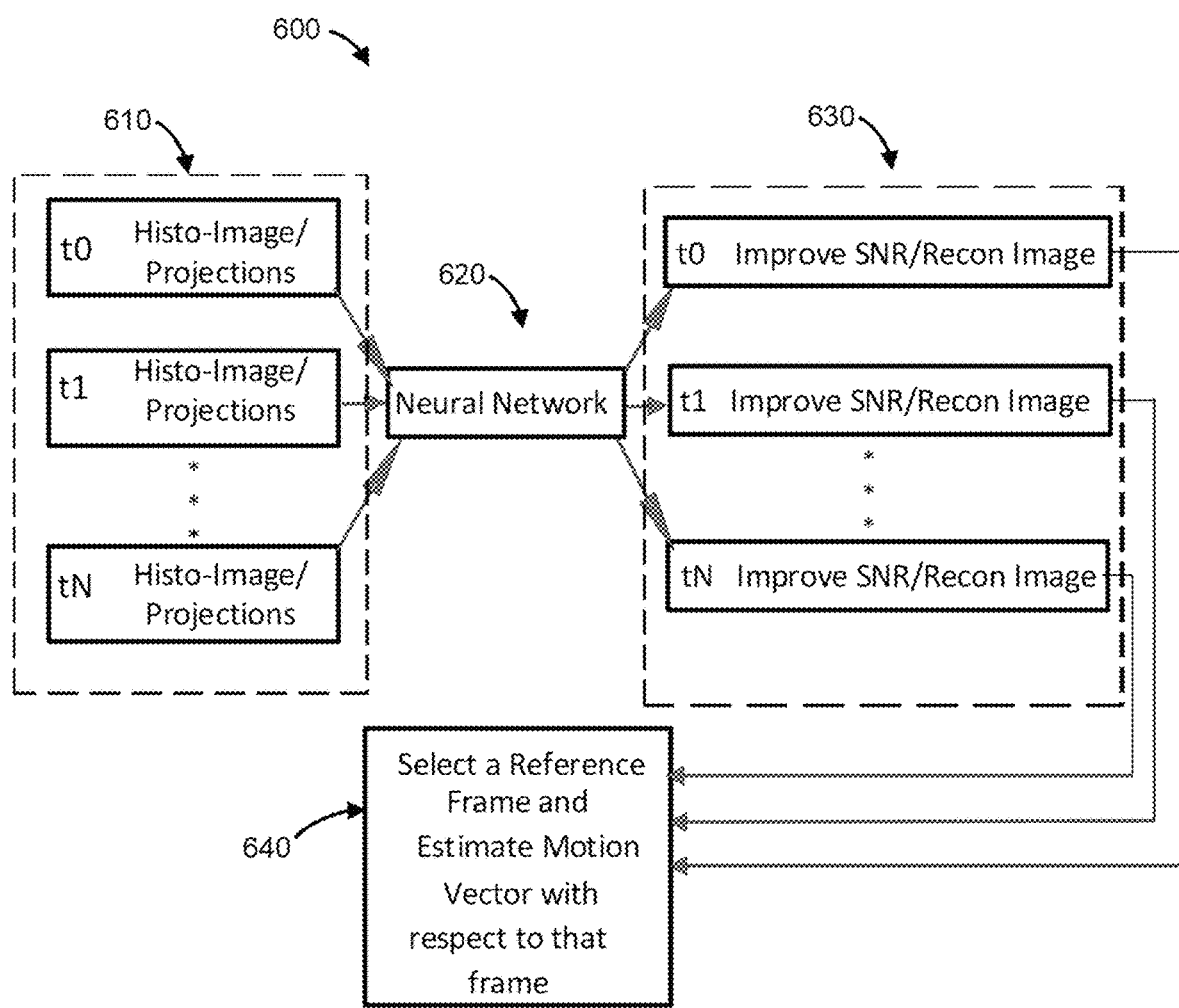
FIG. 6 is a diagram of another example of the method to reconstruct an image, in accordance with some embodiments of the present disclosure.

FIG. 6 is a diagram of an image reconstruction process 600 of another exemplary embodiment of the disclosed feature of estimating motion vectors based on AI processing which is applicable to any motion including cyclic and non-cyclic motion. In the image reconstruction process 600, the PET system 110 is configured to generate a plurality of histo-image frames 610 at a plurality of time frames t0 to tN. Each histo-image at each of the plurality of frames t0 to tN is input to a neural network 620 to produce a reconstructed image frame 630 at each of the frames t0 to tN. One of these AI reconstructed image frame will be selected as a reference frame. The plurality of AI reconstructed image frames 630 can be used by the PET system 110 to produce a motion estimation 640 for each image frame with respect to this reference frame. The motion estimation 640 can be used by the PET system 110 to reconstruct one or more final motion-corrected images (e.g., by combining the motion estimation 640 with the plurality of reconstructed images 630 to produce a final image reconstruction for desired frames using all counts).

In the image reconstruction process 600, at least two histo-images are inputted to the neural network 620 to produce AI reconstructed images that are used to estimate motion for use in motion correction. The at least two histo-images include a plurality of framed images at the various frame times t0 to tN. Histo-projections instead of histo-images could be used. A histo-projection is a precursor to a histo-image which only consists of projection data along certain directions whereas histo-image combines projection data from all directions.

Among various advantages, the embodiments can reconstruct images from measurement data generated by nuclear imaging systems, such as PET scanners, with reduced computational costs compared to conventional systems and methods. For example, the embodiments can reduce the amount of memory required (e.g., memory requirements) to generate reconstructed images. As another example, the embodiments can generate reconstructed images in less time than conventional systems, given the same computational (e.g., processing) power. In some examples, the embodiments can create quantitatively higher quality images than conventional systems and methods.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein can be applied to other embodiments without the use of inventive faculty. The present disclosure is not intended to be limited to the embodiments shown herein, but is to be accorded the widest scope consistent with the principles and novel features disclosed herein.

What is claimed is:

1. A computer-implemented method for generating a motion corrected image comprising:
receiving listmode data collected by an imaging system;
producing two or more histo-image frames or two or more histo-projection frames based on the listmode data;

providing the two or more histo-image frames or two or more histo-projection frames to an Artificial Intelligence (AI) system;

receiving two or more AI reconstructed image frames from the AI system based on the two or more histo-image frames or the two or more histo-projection frames;

identifying one motion free AI reconstructed image frame among the two or more AI reconstructed image frames as a reference image frame; and estimating motion in each of the remaining non-reference AI reconstructed image frames by comparing the image frame data of the non-reference AI reconstructed image frames to the image frame data of the reference image frame.

2. The computer-implemented method of claim 1, further comprising:

generating a motion vector field for each of the remaining non-reference AI reconstructed image frames;

applying motion correction to each of the histo-image frames or the histo-projection frames corresponding to each of the non-reference AI reconstructed image frames using the corresponding motion vector field; and generating motion corrected reconstructed image frames.

3. The computer-implemented method of claim 1, further comprising:

generating a motion vector field for each of the remaining non-reference AI reconstructed image frames; and applying motion correction to each of the non-reference AI reconstructed image frames using the corresponding motion vector field to generate motion corrected reconstructed image frames.

4. The computer-implemented method of claim 1, wherein the motion can be cyclic or non-cyclic motion.

5. The computer-implemented method of claim 1, wherein the two or more histo-image frames are produced based on events and corresponding time-of-flight information in the listmode data and an approximation algorithm.

6. The computer-implemented method of claim 5, wherein the approximation algorithm is a most-likely annihilation algorithm.

7. The computer-implemented method of claim 1, wherein the AI system comprises a neural network trained to generate images from histo-images.

8. The computer-implemented method of claim 1, wherein the two or more histo-image frames comprise a static histo-image and a framed histo-image.

9. The computer-implemented method of claim 1, wherein the two or more histo-image frames comprise framed histo-images at times t0 to tN.

10. A system comprising:

a non-transitory memory for storing listmode data received from an imaging device, wherein the non-transitory memory having a set of instructions stored thereon; and at least one processor communicatively coupled to the memory and configured to execute the set of instructions to:

produce two or more histo-image frames or two or more histo-projection frames based on events and corresponding time-of-flight data and an approximation algorithm;

provide the two or more histo-image frames or two or more histo-projection frames to a neural network;

receive two or more Artificial Intelligence (AI) reconstructed image frames having been processed by the neural network;

identify one motion free AI reconstructed image frame among the two or more AI reconstructed image frames as a reference image frame; and estimate motion in each of the remaining non-reference AI reconstructed image frames by comparing the image frame data of the non-reference AI reconstructed image frames to the image frame data of the reference image frame.

11. The system of claim 10, wherein the set of instructions when executed by the at least one processor further results in the processor to:

generate a motion vector field for each of the remaining non-reference AI reconstructed image frames; and apply motion correction to each of the histo-image frames or the histo-projection frames corresponding to each of the non-reference AI reconstructed image frames using the corresponding motion vector field to generate motion corrected reconstructed image frames.

12. The system of claim 10, wherein the set of instructions when executed by the at least one processor further results in the processor to:

generate a motion vector field for each of the remaining non-reference AI reconstructed image frames; and apply motion correction to each of the non-reference AI reconstructed image frames using the corresponding motion vector field to generate motion corrected reconstructed image frames.

13. The system of claim 10, wherein the motion can be cyclic or non-cyclic motion.

14. The system of claim 10, wherein the approximation algorithm is a most-likely annihilation algorithm.

15. The system of claim 10, wherein the neural network is trained to reconstruct images from histo-images.

16. The system of claim 10, wherein the two or more histo-images comprise framed histo-images at times t0 to tN.

17. The system of claim 10, wherein the two or more histo-images comprise a static histo-image and a framed histo-image and the two or more AI reconstructed images comprise an AI static histo-image and an AI framed histo-image.

18. A non-transitory computer readable medium storing instructions that, when executed by at least one processor, cause the at least one processor to perform operations comprising:

receiving listmode data collected by an imaging system;

producing two or more histo-image frames or two or more histo-projection frames based on the listmode data;

providing the two or more histo-image frames or the two or more histo-projection frames to an Artificial Intelligence (AI) system;

receiving two or more AI reconstructed image frames from the AI system based on the two or more histo-image frames or the two or more histo-projection frames;

identifying one motion free AI reconstructed image frame among the two or more AI reconstructed image frames as a reference image frame; and estimating motion in each of the remaining non-reference AI reconstructed image frames by comparing the image frame data of the non-reference AI reconstructed image frames to the image frame data of the reference image frame.

19. The non-transitory computer readable medium of claim 18, wherein the operations further comprise:
generating a motion vector field for each of the remaining non-reference AI reconstructed image frames; and
applying motion correction to each of the histo-image frames or the histo-projection frames corresponding to each of the non-reference AI reconstructed image frames using the corresponding motion vector field to generate motion corrected reconstructed image frames.

20. The non-transitory computer readable medium of claim 18, wherein the operations further comprise:
generating a motion vector field for each of the remaining non-reference AI reconstructed image frames; and
applying motion correction to each of the non-reference AI reconstructed image frames using the corresponding motion vector field to generate motion corrected reconstructed image frames.

21. The non-transitory computer readable medium of claim 18, wherein the motion can be cyclic or non-cyclic motion.

22. The non-transitory computer readable medium of claim 18, wherein the two or more histo-images are produced based on events and corresponding TOF information in the listmode data and an approximation algorithm.

23. The non-transitory computer readable medium of claim 18, wherein the two or more histo-images comprise framed histo-images at times $t0$ to $tN$.

* * * * *